United States Patent [19]

Knobeloch et al.

[11] Patent Number: 5,198,336
[45] Date of Patent: Mar. 30, 1993

[54] BIOASSAY FOR CHEMICALS WHICH GENERATE PROOXIDANT STATES

[75] Inventors: Lynda M. Knobeloch; George A. Blondin; John M. Harkin, all of Madison, Wis.

[73] Assignee: Wisconsin Alumni Research Foundation, Madison, Wis.

[21] Appl. No.: 348,637

[22] Filed: May 8, 1989

[51] Int. Cl.⁵ .................... C12Q 1/26; C12Q 1/32; G01N 24/00; G01N 21/00
[52] U.S. Cl. .......................... 435/4; 435/25; 435/26; 436/35; 436/164
[58] Field of Search ............. 435/4, 25, 26; 436/35, 436/164

[56] References Cited

U.S. PATENT DOCUMENTS 4,808,517  2/1989  Blondin et al. ................. 435/4

OTHER PUBLICATIONS

Smith et al., Meth. Enz. 105:505–510 (1984).
Lorentzen et al., Biochemistry 16(7): 1467–1473 (1977).
Abstract and accompanying poster "An in vitro mitochondrial bioassay for predicting acute toxicity in fish", Blondin, Knobeloch, Read and Harkin, Cincinnati, OH, May of 1987.
"Use of Mammalian Mitochondrial Electron Transport Particles for the Detection of Toxic Substances in Fresh Water and Evaluation of Chemical Toxicity", Thesis by Lynda Knobeloch submitted to University of Wisconsin-Madison, Winter of 1988–89.

Primary Examiner—Margaret Moskowitz
Assistant Examiner—Stephanie W. Zitomer
Attorney, Agent, or Firm—Quarles & Brady

[57] ABSTRACT

A bioassay making use of submitochondrial particles to test for the presence of toxic substances which induce prooxidant states in vivo. The assay uses complex I of the electron transport enzymes on the submitochondrial particles which are capable of donating electrons to the toxicant in solution. The presence of any activated oxygen species in the assay solution is detected spectrophotometrically by the adrenochrome reaction.

15 Claims, 3 Drawing Sheets

BIOASSAY FOR CHEMICALS WHICH GENERATE PROOXIDANT STATES

This invention was made with the United States government support awarded by the U.S. Geological Survey, Department of the Interior (USGS), Grant Number: 14-08-0001-G1295. The United States government has certain rights in this invention.

FIELD OF THE INVENTION

The present invention relates generally to the field of chemical toxicity testing or toxic testing in the environment and relates, in particular, to a rapid and convenient toxicity screening procedure.

BACKGROUND OF THE INVENTION

In recent years it has been widely recognized that many commercial and industrial chemicals can, even in very low amounts, cause toxic effects on humans, domesticated animals, and fish and wildlife. Such toxicants can be present in trace amounts in pharmaceuticals, food additives, industrial and agricultural products and can produce acute or chronic adverse somatic effects in humans or animals exposed to or ingesting these materials, as well as mutagenic, teratogenic or carcinogenic effects. It has therefore become common place in modern society to test the newly synthesized chemical or products for an array of toxic effects. However, many of these effects are difficult to assess even though they may cause illness in humans or animals exposed to such substances. It also becomes increasingly important to be able to test processed materials or substances of unknown constituency, or food products for the presence of contaminants of a toxic character.

It is therefore quite useful to have assays which can identify toxic substances or detect them in samples of material of unknown constituency. Ideally such assays would be qualitative as well as quantitative indicating the type of chemical substance which is detected if a positive result is obtained from the assay. However the qualitative chemical analysis of an unknown sample of toxic substances is at present a very slow and expensive technological effort. Mixtures of various toxic substances can present special difficulties because of the need to conduct separate analyses for the constituents thereof. The situation can be further complicated when multiple toxic substances are present in a single sample since the interaction between the toxicants can result in additive, synergistic, or antagonistic interactions thus making the results extremely difficult to predict. Nevertheless, even if qualitative analysis is impractical, sensitive quantitative analysis of samples to be screened for the presence of deleterious, even if unknown, toxicants is of great use in determining the safety of substances in the human or animal environment.

One generalized approach to the problem of sensitive testing for the presence of adverse toxic chemicals in a sample is to use biological materials which are extremely sensitive in the assays. These bioassays typically measure the response of a biological preparation or whole organism to challenges from the test chemical or environmental sample of unknown constituents to see if the preparation or organism is affected. Such a bioassay will not identify the chemicals concerned but will quantitatively measure their effect on biological activity. It has been found that data from such bioassay tests correlate well with the effect on laboratory animals and humans when determined by conventional toxicological or epidemiological data. Various prior assays have been based on simple enzymes or group of enzyme tests or on the responses of whole organisms such as bacteria or fish which are exposed to the samples in question. One commercial system utilizes the light output of a bioluminescent bacterium to determine the biological response of the bacterium to toxicological effects of the test chemical or environmental sample being tested.

It has previously been reported by some of the inventors here that a bioassay for toxic substances is practical based on the use of submitochondrial particles. This bioassay using submitochondrial particles, known as the reverse electron transport, or RET assay has been used with another test referred to as the electron transport, ETR, to accurately predict the aquatic and cellular toxicity of a variety of chemicals. The assay is based on the use of submitochondrial particles having an intact mitochondrial membrane containing competent enzymes therein and the use of appropriate antibiotics to block the flow of electrons so that reactions can be selectively driven so as to favor reactions the product of which can be determined spectrophotometrically. A suitable reaction which may be catalyzed using the RET process is a conversion of NAD plus to NADH. The presence of toxic substances in the test sample which interfere with the functioning of competent mitochondrial enzymes or the competency of the mitochondrial lipid membrane itself would disrupt the functioning the of the RET electron flow system, the disruption of which can be detected by the change in photometric response of the solution. This bioassay is described in U.S. Pat. No. 4,808,517.

Prooxidants constitute another category of toxic substances which are capable of exerting toxicity on living organisms. Biological scientists have recently become aware that such chemicals exert their acute toxicity, mutagenicity and carcinogenicity by inducing a prooxidant state in vivo. When a prooxidant state is induced on a cellular level, the cellular concentration of activated forms of oxygen increases. The major forms of activated oxygen are the superoxide anion radical ($\cdot O_2^-$) and its conjugate acid, the hydroperoxy radical ($HO_2 \cdot$), singlet oxygen ($O_2^1$), hydrogen peroxide ($H_2O_2$) and the hydroxyl radical ($HO \cdot$). Each of these three radicals is highly reactive and has the capacity to attack cellular lipid membranes, proteins, and DNA causing their oxidative degradation. The biological consequences of the prooxidant state include inhibition of gap-junction communications between cells, sister chromatid exchanges, mutations of nuclear and mitochondrial DNA, carcinogenesis, aging, and cell death. To avoid these damaging effects, all aerobic cells have developed elaborate, multiple level defensive systems. These protective defensive systems are based on the ability of antioxidants such as vitamins A, C, and E and glutathione or enzymes such as superoxide dismutase, catalase and peroxidase to destroy the free radicals or oxidants before they can attack cellular components and exert their toxic effects.

In a normal healthy cell a delicate balance exists between activated hydrogen radicals produced as a minor by-product of aerobic respiration and other metabolic processes and the removal of these radicals by antioxidants with little oxidative damage resulting from their brief existence. However, this balance can be upset by an excessive production of free radicals or a defect in the defensive system of the cell. Exposure to such diverse chemicals as the herbicides paraquat and diquat, the anti-cancer drug adriamycin and the redox dye sulfonazo III can increase the rate of production of oxygen free radicals in vivo resulting in the creation of activated forms of oxygen faster than the cell can process them. The result is a prooxidant state which is believed responsible for the deadly lung damage seen in people exposed to paraquat, the kidney damage associated with diquat exposure, and the cardiotoxicity of adriamycin administered in cancer chemotherapy.

Because of the severe consequences of exposures to such chemicals which can induce the prooxidant state it is important that rapid and sensitive methods be developed for the detection of these substances in environmental samples or to identify new or existing chemicals with this ability. Although researchers have been able to demonstrate the ability of individual substances to generate prooxidant states using elaborate cell culture or subcellular systems, no rapid screening tests for general applicability to chemicals which induce a prooxidant state are heretofore available.

SUMMARY OF INVENTION

The present invention is summarized in that a method for assaying for the presence of toxicants capable of inducing a prooxidant state in the sample is detected by spectrophotometric analysis comprising the steps of preparing a suspension including at least portions of mitochondrial membranes having competent electron transport enzyme complex I thereon; adding to the suspension and assay medium including buffer salts, NADH, and a substance catalyzable by free oxygen radicals into a state which can be detected by photo spectrometrical analysis; adding a quantity of the test sample; and measuring the spectrophotometric change caused by the presence of the prooxident chemical.

It is an object of the present invention to provide a method for identification and detection of toxic substances which induce a prooxidant state in vivo so that environmental, industrial and pharmaceutical samples can be tested in an economical and efficient manner based on a sensitive bioassay technique.

It is another object of the present invention to provide a kit for use in performing a bioassay to identify and detect prooxidant inducing toxic chemicals. Such a kit includes suitable substrates and materials so that assays for such toxic substances can be quickly and easily performed.

Other objects, advantages, and features of the following invention will become apparent from the following specification.

BRIEF DESCRIPTION OF THE DRAWING FIGURE

DESCRIPTION OF THE PREFERRED EMBODIMENT

Figure 1:
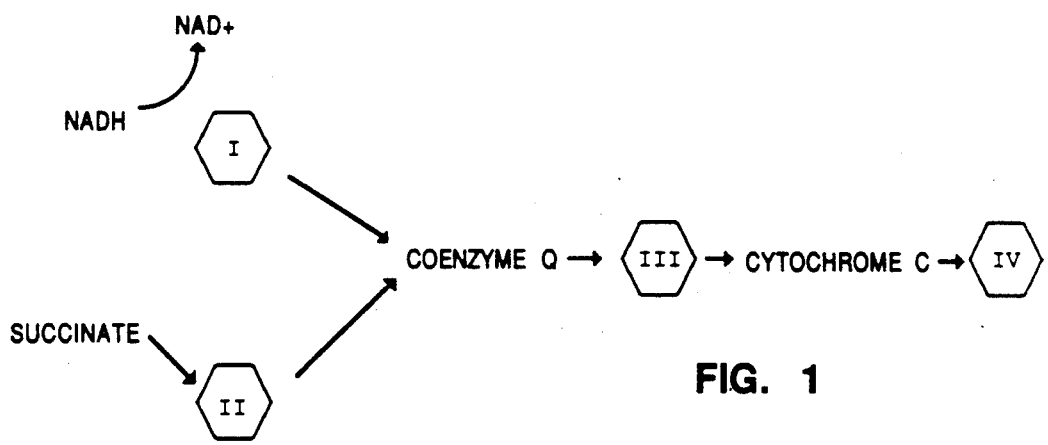
FIG. 1 illustrates in schematic fashion the normal flow of reaction products through the enzyme complexes of the mitochondrial electron transport system.

The method and kit utilizing the bioassay of the present invention are intended to make use of mitochondrial preparations as biological assay tools intended to identify or detect the presence of a specific class of toxicants in samples of unknown constituency. Such mitochondrial preparations have been described before and represent an attractive compromise between the over-simplification of most in vitro assays and the time-consuming and expensive nature of sophisticated assays conducted with whole organisms. The test described here has high sensitivity and is selective to a specific class of toxic chemicals acting through a common modality of toxicity.

Mitochondria are cellular organelles which are often characterized as being the biochemical power plant of eukaryotic cells since mitochondria have the basic biochemical enzymes required to oxidize nutrients at the cellular level to produce energy for the cell. In addition, mitochondria have enzymes performing a variety of other metabolic and ion transfer functions within the cell which require a highly organized system of enzymes in membrane structures. The enzymes of critical interest are those in the electron transport cascade which are carried on the inner membrane of mitochondria. The electron transport chain involves the flow of electrons to create energy storing and utilizing molecules within the cell. For a certain class of chemicals, i.e. those which induce a prooxidant state in vivo in cells, the mechanism by which the toxic chemical acts is to withdraw electrons supplied during the mitochondrial respiratory electron transport chain to form an unstable intermediate. These unstable intermediates are free radicals which can interact with elemental dioxygen to produce activated forms of oxygen which can damage cellular processes. It is for this reason that the presence of at least portions of the mitochondrial electron transport enzyme cascade are useful in an in vitro assay to detect the presence of such prooxidant state inducing toxicants.

The present invention is directed toward the creation of a bioassay and a mitochondrial test preparation kit to test for the presence of such prooxidant, or to identify pure compounds with this ability, inducing compounds in a sample of unknown character utilizing at least portions of mitochondrial enzymes having a competent electron transport enzyme complex I thereon. Therefore, to practice this invention, it is appropriate to have a mitochondrial preparation that includes the necessary competent mitochondrial in a membrane carrying the appropriate enzyme complex thereon. The source of the mitochondrial or submitochondrial particles used in the assay are not critical. Conventional mitochondrial preparations such as rabbit heart, rat liver, rat kidney, rat brown fat, or unfractionated beef heart mitochondria, may be used as well as whole or partial preparations of any such mitochondria within the present invention. It could also be possible, in theory, to isolate complex I of the electron transport chain from the mitochondrial background in which exists and to use that complex alone within the bioassay of the present invention. The preferred mitochondrial preparation for use in the invention is, however, submitochondrial particles. The submitochondrial particles are bilayer lipid vesicles resulting from micell formation from the fragments of cristae membranes when whole mitochondria are ruptured. In essence, whole mitochondria from a biological source are ruptured by sonication or detergents such as digitonin or treatment in a French press, separated from cytosolic residues by centrifugation, and the membrane segments are then allowed to reform into vesicles which model the behavior of the intact inner membrane of mitochondria. Such mitochondrial particles have the asset, in addition to modeling well the mitochondrial behavior of the enzymes in the electron transport chain, that they may be prepared and frozen or freeze-dried for storage in quantity so that aliquots of the submitochondrial preparation can be available for use in conducting toxic and bioassays over a long period of time.

The preparation of submitochondrial particles for use in the present invention therefore begins with the preparation of whole mitochondria. Whole mitochondria from any available source can be used. Beef-heart mitochondria are relatively easy to prepare by the method described by Blair *Methods in Enzymology* 10:78-81 (1967). The submitochondrial particles themselves can then be prepared from either fresh or frozen mitochondria preferably by the method described by Hansen and Smith in *Biochem. Biophys. Acta* 81:214-222 (1964). Such mitochondrial particles once prepared can be stored or shipped frozen in a preserving mixture such as known to one of ordinary skill in the art. Alternatively, the mitochondrial particles can be freeze dried by a process also well known to the art. Frozen preparations simply need to be thawed for use while freeze dried preparations can simply be reconstituted by insertion into an assay medium shortly before use.

To understand the operation of an assay conducted in accordance with the present invention, it is necessary to consider the enzyme complexes conventionally recognized in the electron transport chain in mitochondria. As can be viewed in FIG. 1, enzyme complex I catalyzes the reduction of NADH to NAD+ at the same time that ADP is converted to ATP in the reaction. Electron flow is then from enzyme complex I toward co-enzyme Q and from thereafter to enzyme complex III. Meanwhile, succinate is oxidized in enzyme complex II to produce an alternative source of electron flow into the electron transport cascade. From co-enzyme Q, the electron flow proceeds through enzyme complex III to cytochrome C to enzyme complex IV, which ultimately transfers electrons to molecular oxygen. Each of the enzyme complexes in the electron transport cascade can be inhibited selectively by individual toxicants and these toxicants can be used in in vitro assays to selectively inhibit electron flow through undesired paths. For example, electron flow from complex I to co-enzyme Q can be inhibited by rotenone, complex II can be inhibited by thenoyltriflouroacetone, and electron flow from co-enzyme Q to complex III can be inhibited by antimycin A. It is particularly the inhibitors which prevent electron flow away from enzyme complex I, such as rotenone or antimycin that are useful in the practice of the present invention in which it is desired that there be free electrons present in complex I for reasons that will become clear in the following discussion.

Figure 2:
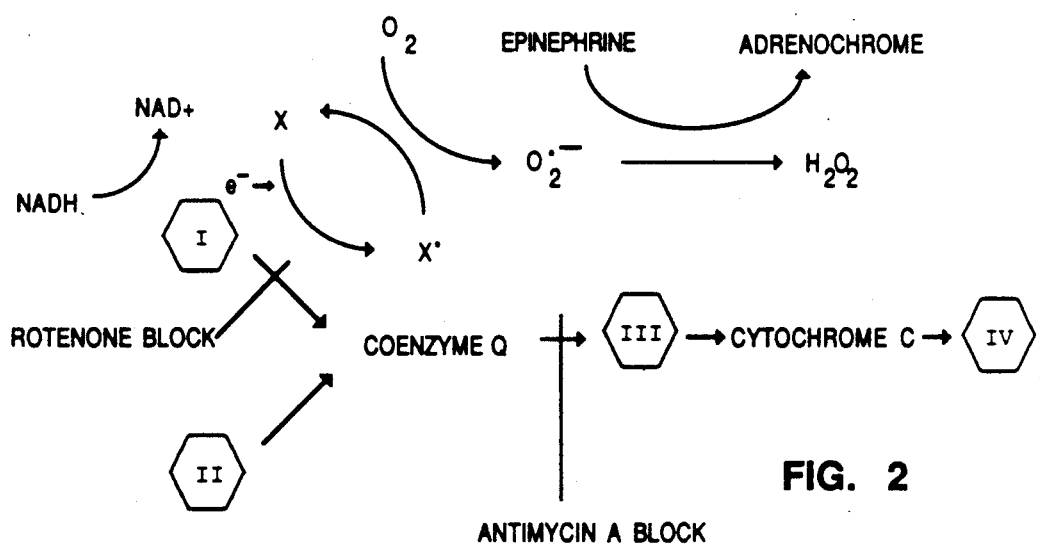
FIG. 2 illustrates the altered system created in the method of the preferred embodiment described below.

In essence, the facilitated electron withdrawal technique described in the assay of the present invention is designed to create an excess of electrons present in enzyme complex I which will then be "leaked" in the presence of a toxicant which can induce a prooxidant state to convert the toxicant into its free radical and active form. The facilitated electron withdrawal procedure is schematically illustrated in FIG. 2. As can be seen, complex I received electrons from the oxidation of NADH to NAD+. The flow of those electrons toward complex III of the electron transport cascade is inhibited by the presence of rotenone and by the presence of antimycin. The excess electrons then present in complex I act on the prooxidant inducing toxicant X, if it is present, to drive it into a free radical state X·. It is the conversion of the free radical state X· of the toxicant back into X that causes the forms of activated oxygen, such as $\cdot O_2^-$ to be created. A redox indicator, such as epinephrine, is also present in the sample which is reduced by the activated form of oxygen into adrenochrome. Adrenochrome has a characteristic brown color which allows the creation of that reduction product to be determined spectrophotometrically within the reaction.

In addition to the mitochondrial preparation, an assay medium is also necessary to perform the bioassay using the facilitated electron withdrawal procedure of the present invention. The assay should contain suitable buffers, such as a HEPES buffer, and should contain the necessary substrates and inhibitors appropriate to drive the desired enzyme effect illustrated in FIG. 2. It is appropriate to deplete the submitochondrial particles of their content of superoxide dismutase. This enzyme which is normally present in the matrix of mitochondrial membrane catalyzes the destruction of superoxide radicals. Therefore the sensitivity of this test is increased by depleting the content of superoxide dismutase which would otherwise reduce the concentration of superoxide radicals present in the experimental solution. Depletion of superoxide dismutase may be conveniently accomplished by washing the particles with ETDA, a metal chelator which removes the manganese co-factor from superoxide dismutase.

The assay medium may include an inhibitor to prevent enzyme activity not desired in the assay of the present invention. Inhibitors such as rotenone and antimycin A can be used individually or collectively to inhibit electron flow from complex I to co-enzyme Q or from co-enzyme Q to complex III respectively. It is also envisioned that other suitable enzyme complex inhibitors, such as cyanide or amytal, could also be used in the assay of the present invention or coenzyme Q could be removed from the particles by pentane extraction.

The assay medium of the present invention also requires a redox indicator. The redox indicator should be a substance which can be reduced or oxidized in such a fashion that the presence of the reaction product can be measured spectrophotometrically. Possible redox indicators include ferricytochrome C or nitroblue tetrazolium. However, the preferred redox indicator is epinephrine which, as indicated above, is oxidized to adrenachrome which has a characteristic brownish color which could easily be detected spectrophotometrically.

The assay medium of the present invention also requires a source of electrons. Illustrated in FIG. 2 is the source of electrons as NADH. An NADH generating could also be used to provide electrons or other sources may be used to provide electrons. For example, assuming that the flow of electrons from co-enzyme Q is blocked by antimycin, it would be possible to introduce excess electrons into enzyme complex II from which they would flow back into enzyme complex I. In that instance succinate could be used as a source of electrons. Also in that instance, the electron leak from ubiquinone could be used in the absence of complex I all together.

One advantage of the assay method of the present invention is that the reactants can simply be admixed in a common receptacle, since the reaction can be controlled by withholding the source of electrons until desired. Therefore, all of the other constituents can be added to the experimental solution and prepared for use with the addition of the electron source delayed until the sample is ready to be introduced into the spectrophotometer. This allows the assay to be conveniently performed in a spectrophotometer cuvette such as a conventional 1 cm optical length cuvette, although it has been found that other cuvettes are also usable within the present invention. Using this technique, the assay can be conducted by adding the mitochondrial preparation, the buffer, the mitochondrial enzyme inhibitor and the redox indicator all to the cuvette. The assay sample can also directly be added to this combination. A base line reading of optical character can be determined spectrophotometrically this time to determine a base line level. Then the source of electron flow into the enzyme complex can be added, such as by the addition of NADH. At this time the activity of the toxicant inducing prooxidant activity will become apparent due to the creation of the redox indicator reaction product such as the brown adrenachrome. This reaction product can thus be determined spectrophotometrically so that the results of the assay can be determined.

In general the process of the present invention can be used to determine the presence or absence of toxicants which induce prooxidant states in samples from any of a wide variety of environmental sources or from samples of any other materials in which it is desired to test for the presence or absence of these toxic substances. The results can be used both qualitatively and quantitatively to determine the concentration of such toxicants in a potentially contaminated source or to compare the toxicity of various toxicants. The method has proved useful and practical for a number of prooxidant inducing toxicants and certainly the assay would prove effective to detect and identify other such toxicants the action of which has yet to be characterized.

EXAMPLE OF PRACTICE OF THE PRESENT INVENTION

The practice of the present invention began with the creation of submitochondrial electron transport particles (ETP) isolated from beef hearts. These are also referred to as submitochondrial particles. The mitochondria were isolated from bovine heart muscle by the method of Blair, supra. The superoxide dismutase-depleted ETP particles were prepared by sonicating the thawed mitochondria for two minutes in a medium containing 0.25M sucrose and 2 mM EDTA, pH 7.5, at a protein concentration of 25 mg per ml. The result was diluted with an equal volume of 0.25M sucrose and adjusted to a pH of 7.5 after which it was centrifuged for 40 minutes at 105,000×g. The resulting ETP particles were washed in ten volumes of 0.25M sucrose and sedimented by centrifugation. After treatment the ETP particles were stored frozen in buffered 0.25M sucrose at a protein concentration of 20 mg per ml.

The test medium contained 50 mM HEPES buffer, 1.5 mM epinephrine and 0.4 uM antimycin. The medium was adjusted to a pH of 7.2 with 5M potassium hydroxide and dispensed in 1.8 ml aliquots into 1-CM path length glass cuvettes. Either aqueous diluent or the test sample was added in a volume of 20-50 ul so that the final concentration ranged between 0 and 100 ug per ml. Following the addition of 0.5 mg of the SOD-depleted ETP particles suspended in a 0.1 ml 50 mM HEPES buffer, the cuvettes were covered with parafilm and inverted three times to mix the contents. First a base line absorbance reading was taken by the spectrophotometer set for 480 nm.

After the base line reading was taken, the reaction was started by adding 50 ul of 5 mM NADH. The final absorbance readings were then taken after a 10 minute incubation at room temperature. The final absorbance readings were used to calculate a lowest observable effect concentration (LOEC) for each of the chemicals tested. The LOEC is defined as the concentration which gives a response three standard deviations above the mean control value. It is intended that the LOEC value be analogous to the limited detection value used for environmental samples subject to conventional analysis.

Figure 3:
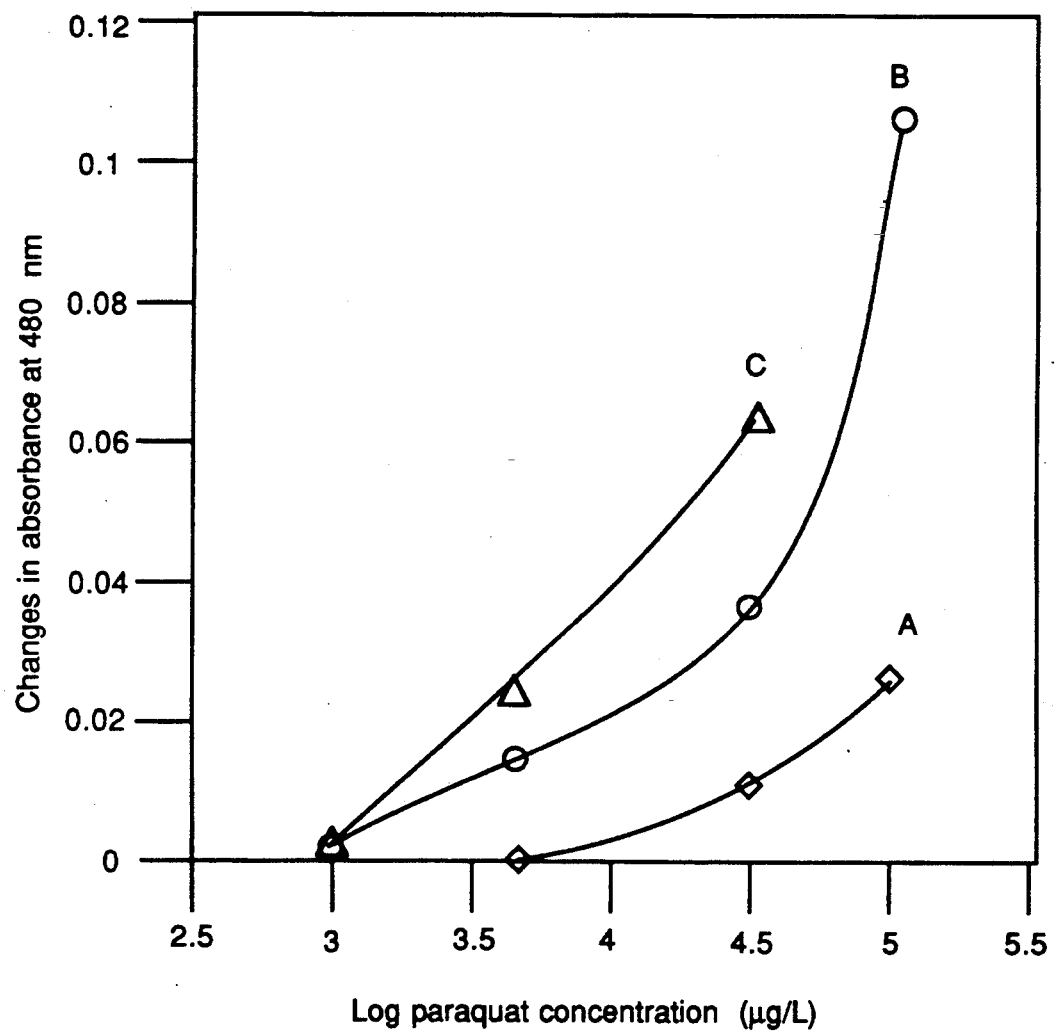
FIG. 3 is a graphical illustration of results obtained using the method of the present invention.

FIG. 3 is a graphical illustration of the experimental results for this assay tested with several dilutions of paraquat. The paraquat was tested with and without the addition of antimycin A or rotenone. The curve labeled A contained neither antimycin A nor rotenone while the curve labeled B included antimycin A at 0.2 ug per ml antimycin A and the curve labeled C contained 0.2 ug per ml rotenone. The curve indicates that the inhibition of electron transport induced by the respiratory toxins increases the rate at which paraquat can draw electrons from the electron transport cascade. As the paraquat is reduced to an unstable free-radical intermediate it rapidly transfers electrons to molecular dioxygen and reverts to its ground state. This redox cycling procedure produces the superoxide anion radical detected by the adrenochrome reaction which is quantified by the increase in absorbance at 480 nm.

Figure 4:
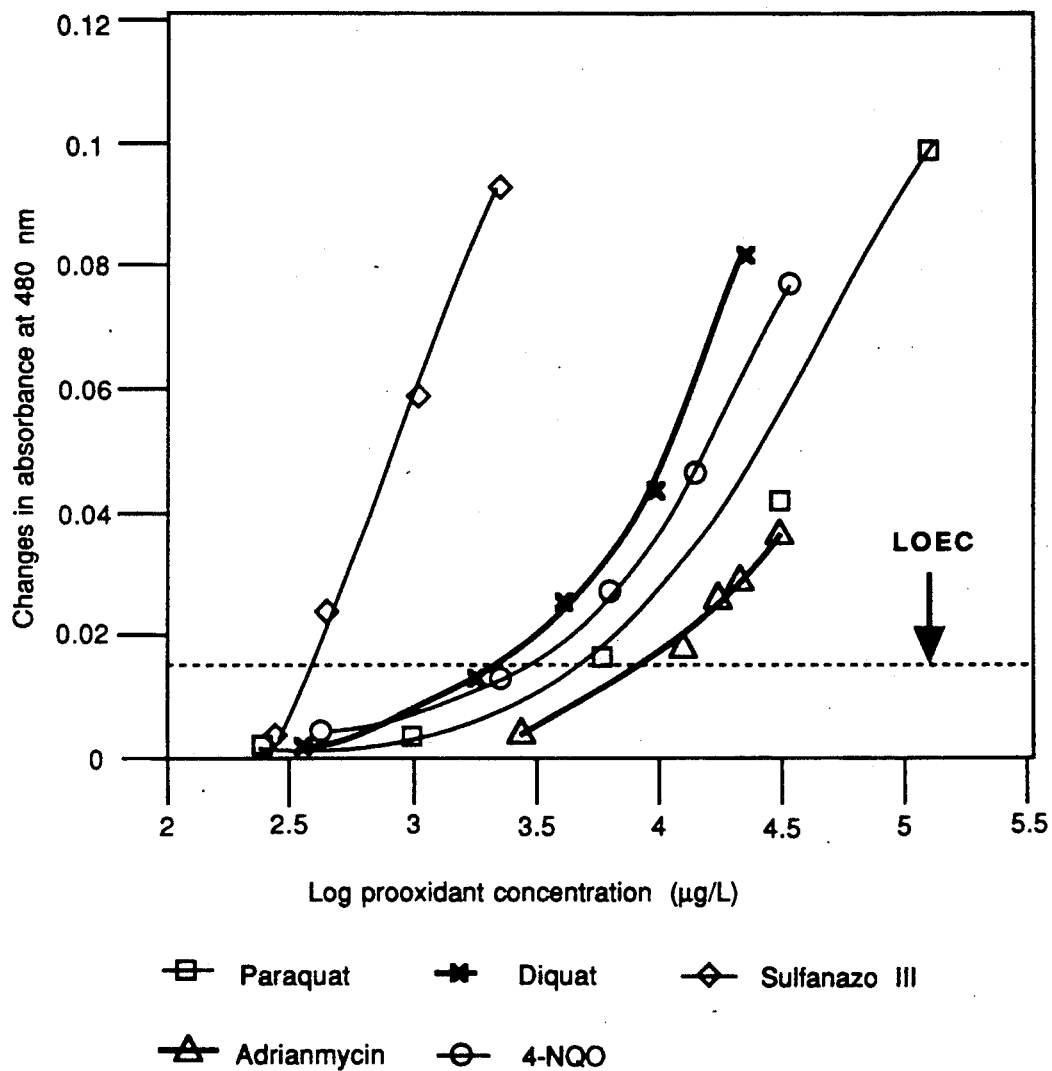
FIG. 4 is another graphical illustration of such results.

FIG. 4 illustrates the results of experimental runs which were conducted with the chemicals paraquat, diquat, sulfonazo III, adriamycin, and 4-nitroquinoline-N-oxide. These results provide a relative measure of the potency of these five agents to induce a prooxidant state with sulfonazo III being the strongest inducer of the prooxidant states and adriamycin being the weakest. The lowest observable effect concentrations (LOEC) for the five prooxidant inducing toxicants is given in the following table. All experiments summarized in this table and in FIG. 4 were conducted with 2 ml HEPES buffer, a pH of 7.2, 1.5 mM epinephrine, 0.2 ug per ml antimycin A, 0.5 mg ETP, 125 uM NADH and 0 to 10 ug per ml of the test toxicant.

TABLE

| Toxicant | LOEC |
| --- | --- |
| Sulfonazo III | 320 ug/l |
| Diquat | 1600 ug/l |
| 4-Nitroquinoline-N-oxide | 1600 ug/l |
| Paraquat | 3500 ug/l |
| Adriamycin | 6300 ug/l |

The results indicate that the assay is effective for determining a wide variety of toxicants which induce prooxidant state and further demonstrate that the resulting observed response from spectrophotometric analysis of the experimental sample is due to the creation of such a prooxidant state.

It is understood that the present invention is not limited to the particular embodiment thereof described above, but embraces all such modified forms thereof as come within the scope of the following claims.

We claim:

1. A method of assaying for the presence of prooxidant state inducing toxicants in a sample by spectrophotometric analysis comprising the steps of
    (a) preparing a suspension including at least portions of mitochondrial membranes having a competent electron transport enzyme complex I thereon;
    (b) adding to the suspension an assay medium including buffer salts; a selective mitochondrial enzyme inhibitor to inhibit electron flow to other enzyme complexes; and epinephrine;
    (c) adding a quantity of the sample being tested;
    (d) taking spectrophotometric baseline samples;
    (e) adding a source of electron flow for forward electron transport into the enzyme complex I whereby an excess of electrons is created in enzyme complex I; and
    (f) measuring the spectrophotometric response of the reaction to measure any increase in the presence of the reaction product of epinephrine, thus indicating the prooxidant activity of the sample.

2. A method as claimed in claim 1 wherein the suspension of at least portions of mitochondrial membranes includes submitochondrial particles.

3. A method as claimed in claim 1 wherein the mitochondrial membranes have been depleted in their content of superoxide dismutase.

4. A method as claimed in claim 1 wherein the mitochondrial inhibitor is selected from the group consisting of antimycin A, rotenone, cyanide, and amytal.

5. A method as claimed in claim 1 wherein the redox indicator is epinephrine.

6. A method as claimed in claim 1 wherein the source of electron flow is NADH.

7. A method as claimed in claim 1 wherein the source of electron flow is succinate.

8. A kit for use in spectrophotometrically assaying for the presence in a sample of toxicants inducing prooxidant states comprising
    a suspension of a mitochondrial membrane fraction carrying thereon competent enzymes of complex I of the electron transport cascade;
    an assay medium including a buffer salt and epinephrine, both selected so that the delivery of electrons to the enzyme complex will result in conversion of epinephrine to its reaction product only in the presence of a prooxidant inducing toxicant; and
    a source of electron flow for forward electron transport into enzyme complex I whereby an excess of electrons is created in enzyme complex I and the electron flow is sufficient to cause the reaction to create the reaction product of epinephrine in the presence of a prooxidant inducing toxicant.

9. A kit as claimed in claim 8 wherein the mitochondrial membrane fraction is submitochondrial particles.

10. A kit as claimed in claim 8 wherein the mitochondrial enzyme fraction has been depleted in its content of superoxide dismutase.

11. A kit as claimed in claim 10 wherein the assay medium further includes a selective mitochondrial enzyme inhibitor to restrict electron flow through the electron transport cascade.

12. A kit as claimed in claim 11 wherein the mitochondrial enzyme inhibitor is selected from the group consisting of antimycin A, rotenone, cyanide, and amytal.

13. A kit as claimed in claim 8 wherein the redox indicator is epinephrine.

14. A kit as claimed in claim 8 wherein the source of electron flow is NADH.

15. A kit as claimed in claim 8 wherein the source of electron flow is succinate.

* * * * *